(12) United States Patent
Zanini

(10) Patent No.: US 11,408,877 B2
(45) Date of Patent: Aug. 9, 2022

(54) OPTIMIZATION OF THE SPATIAL DISTRIBUTION OF AIR QUALITY MEASUREMENT MEANS

(71) Applicant: ELICHENS, Grenoble (FR)

(72) Inventor: Paolo Zanini, Grenoble (FR)

(73) Assignee: ELICHENS, Grenoble (FR)

( * ) Notice: Subject to any disclaimer, the term of this patent is extended or adjusted under 35 U.S.C. 154(b) by 123 days.

(21) Appl. No.: 16/606,201

(22) PCT Filed: Apr. 17, 2018

(86) PCT No.: PCT/FR2018/050966
§ 371 (c)(1),
(2) Date: Oct. 17, 2019

(87) PCT Pub. No.: WO2018/193205
PCT Pub. Date: Oct. 25, 2018

(65) Prior Publication Data
US 2020/0132650 A1    Apr. 30, 2020

(30) Foreign Application Priority Data
Apr. 19, 2017   (FR) ...................................... 1753393

(51) Int. Cl.
*G01N 1/22* (2006.01)
*G01N 21/3504* (2014.01)
(Continued)

(52) U.S. Cl.
CPC ..... *G01N 33/0075* (2013.01); *G01N 21/3504* (2013.01); *G06T 17/20* (2013.01)

(58) Field of Classification Search
CPC ........... G01N 33/0075; G01N 21/3504; G01N 21/359; G06F 30/13; G06F 17/18;
(Continued)

(56) References Cited

U.S. PATENT DOCUMENTS 6,829,568 B2 * 12/2004 Julier ...................... G06F 17/18
702/189
6,980,926 B1 * 12/2005 O'Brien, Jr. ........ G06K 9/00523
702/179
(Continued)

OTHER PUBLICATIONS

W.F. Caselton et al, Optimal monitoring network designs, Statistics & Probability Letters, vol. 2, No. 2, Aug. 1, 1984, pp. 223-227. (Year: 1984).*
(Continued)

*Primary Examiner* — Jeffrey P Aiello
(74) *Attorney, Agent, or Firm* — TraskBritt

(57) ABSTRACT

A system, for measuring a physical quantity representative of air quality in an observation zone, comprises a mapping with a set (V) of modeled values representative of the physical quantity; means for measuring the physical quantity and possessing N positions or N trajectories in the observation zone to exhibit a spatial distribution ($S_{opt}$); and means for calculating $S_{opt}$. The calculating means are configured to construct a mesh comprising G points in the observation zone; calculate, for a given spatial distribution, an estimator ($\hat{V}$) of the set V for each of the G points in the mesh; calculate a cost function representative of the difference or of the likelihood between $\hat{V}$ and the V values extracted at the G points; and extract the $S_{opt}$ to minimize or maximize the cost function.

18 Claims, 8 Drawing Sheets

(51) Int. Cl.
*G01N 33/00* (2006.01)
*G06T 17/20* (2006.01)

(58) Field of Classification Search
CPC ............... G06F 17/10; G06T 17/20; G06T 2207/20012; Y02A 90/10
USPC ..... 73/1.06; 702/13, 22–23, 179–181; 703/2
See application file for complete search history.

(56) References Cited

U.S. PATENT DOCUMENTS

| | | | | |
|---|---|---|---|---|
| 7,363,191 | B2* | 4/2008 | Spiesberger | G01S 5/02 |
| | | | | 702/142 |
| 2008/0103717 | A1* | 5/2008 | Hel-Or | G06T 5/002 |
| | | | | 702/107 |
| 2012/0086596 | A1* | 4/2012 | Insanic | G01S 13/951 |
| | | | | 342/26 D |
| 2017/0185057 | A1* | 6/2017 | Ashdown | G06F 30/20 |
| 2020/0132650 | A1* | 4/2020 | Zanini | G06T 17/20 |

OTHER PUBLICATIONS

Wei Yi et al, A Survey of Wireless Sensor Network Based Air Pollution Monitoring Systems, Sensors, vol. 15, No. 12, Dec. 12, 2015, pp. 31392-31427. (Year: 2015).*

International Search Report and International Written Opinion for International Application PCT/FR2018/050966, dated Aug. 13, 2018, 11 pages (not including translation).
W.F. Caselton et al, Optimal monitoring network designs, Statistics & Probability Letters, vol. 2, No. 2, Aug. 1, 1984, pp. 223-227.
Wei Yi et al, A Survey of Wireless Sensor Network Based Air Pollution Monitoring Systems, Sensors, vol. 15, No. 12, Dec. 12, 2015, pp. 31392-31427.
Ahmed Bourbrima et al, Optimal Deployment of Wireless Sensor Networks for Air Pollution Monitoring, 2015 24th International Conference on Computer Communication and Networks (ICCCN), Aug. 1, 2015, pp. 1-7.
Murty R N et al, CitySense: An Urban-Scale Wireless Sensor Network and Testbed, Technologies for Homeland Security, 2008 IEE Conference on, IEEE, May 12, 2008, pp. 583-588.
Donald J. Chmielewski et al, On the theory of optimal sensor placement, AIChE Journal, vol. 48, No. 5, May 1, 2002, pp. 1001-1012.
Berkowicz et al., "Modeling traffic pollution in streets", Ministry of Environment and Energy, National Environmental Research Institute, (Jan. 1997) 53 pages.
Berkowicz, "OSPM—A parameterised street pollution model", Environmental Monitoring and Assessment, vol. 65, Issue 1/2, (Nov. 2000) pp. 323-331.
CPCB (Central Pollution Control Board), "Guidelines for Ambient Air Quality Monitoring" National Ambient Air Quality Monitoring, Series: NAAQMS, Ministry of Environment & Forests, (Apr. 2003) 164 pages.

\* cited by examiner

OPTIMIZATION OF THE SPATIAL DISTRIBUTION OF AIR QUALITY MEASUREMENT MEANS

CROSS-REFERENCE TO RELATED APPLICATIONS

This application is a national phase entry under 35 U.S.C. § 371 of International Patent Application PCT/FR2018/050966, filed Apr. 17, 2018, designating the United States of America and published in French as International Patent Publication WO 2018/193205 A1 on Oct. 25, 2018, which claims the benefit under Article 8 of the Patent Cooperation Treaty to French Patent Application Serial No. 1753393, filed Apr. 19, 2017.

TECHNICAL FIELD

This disclosure relates to a system for measuring at least one physical quantity representative of the quality of the air in an observation zone.

In particular, this disclosure finds its application in the monitoring and the control of the quality of the air in urban zones.

BACKGROUND

A measurement system known from the prior art, in particular, from the document "*Guidelines for Ambient Air Quality Monitoring*" drawn up by the CPCB (Central Pollution Control Board) of the ministry of the environment of the government of India, dated April 2003 (hereinafter D1), comprises a set of air quality measurement stations. D1 mentions (cf. § 4.2.2) criteria for selecting the locations of the measurement stations in the observation zone. However, D1 specifies (cf. § 4.2.2.a) that it is difficult to know in advance whether the selected locations will reflect and give an account of the quality of the air in the observation zone. Hence, D1 proposes (cf. § 4.2.2.a) to perform prior measurements to verify the relevance of the locations.

Such a measurement system of the prior art is not entirely satisfactory, in particular, when one wishes to increase the spatial resolution of the measurements. The solution proposed by D1 is very tedious and expensive when the measurement stations exhibit a high spatial density in the observation zone.

BRIEF SUMMARY

This disclosure is aimed at wholly or partly remedying the aforementioned drawbacks. To this effect, the subject of the present disclosure is a system for measuring at least one physical quantity representative of the quality of the air in an observation zone, the system comprising:
a mapping of the observation zone, comprising a set, denoted V, of modeled values representative of the physical quantity;
means for measuring the physical quantity, possessing a number N of positions or a number N of trajectories in the observation zone, the N positions or the N trajectories being intended to exhibit a spatial distribution, denoted $S_{opt}$, in the observation zone; and
means for calculating the spatial distribution $S_{opt}$, configured to:
construct a mesh of the observation zone, the mesh comprising a number G of points;
calculate, for a given spatial distribution, denoted S, of the N positions or of the N trajectories, an estimator of the set V, denoted $\hat{V}$, for each of the G points of the mesh;
calculate a cost function, denoted $\varphi(S)$, representative of the difference or of the likelihood between $\hat{V}$ and the modeled values, denoted $\overline{V}$, of the set V, which are extracted at the G points of the mesh; and
extract the spatial distribution $S_{opt}$, which minimizes or maximizes the cost function depending on whether the cost function is representative of the difference or of the likelihood between $\hat{V}$ and $\overline{V}$.

Thus, such a measurement system according to the present disclosure makes it possible to obtain measurements reflecting and giving an account of the quality of the air in the observation zone, permitting a greater spatial resolution than the prior art, while circumventing local prior measurements. Indeed, such a mapping and such calculation means allow, in conjugation, the extraction of an optimal spatial distribution of the measurement means on the basis of modeled values.

By "mapping" is meant a spatial representation of the modeled values, which can be, for example, two-dimensional (2D) or three-dimensional (3D).

By "representative of the physical quantity" is meant that the modeled values represent the physical quantity directly, or represent the physical quantity indirectly by correlation.

N is a natural integer number.

The "N positions" of the measurement means are defined by spatial coordinates, for example, cartesian coordinates (x, y, z).

The "N trajectories" of the measurement means are N sets of T successive positions over time. The N trajectories are defined by spatial coordinates, for example, cartesian coordinates (x, y, z), and by a temporal component ($t_i$), i lying between 1 and T.

By "spatial distribution" is meant the distribution of the N positions (or of the N trajectories) in the space of the observation zone. It is possible to speak of volumetric or density volumetric distribution in the 3D case.

By "mesh" is meant the spatial discretization of the observation zone.

By "estimator" is meant a statistical estimator where the N positions (or the N trajectories) are random variables.

By "cost function" is meant any function capable of quantifying the coherence between $\hat{V}$ and $\overline{V}$. One also speaks of objective function.

The measurement system according to the present disclosure can comprise one or more of the following embodiments.

According to an embodiment of the present disclosure, the calculation means are configured to calculate the estimator of the set V according to the formula:

$$\hat{V}_j = \frac{\sum_{i=1}^{N} V_i w_{ij}}{\sum_{i=1}^{N} w_{ij}}, \ j \in [\![1, G]\!]$$

where:
$V_i$ are the modeled values of the set V, which are extracted for the positions or for the trajectories of the measurement means exhibiting the given spatial distribution S, and
$w_{ij}$ is a transfer function going between $s_i$ and $m_j$, where $s_i$ are the positions or the trajectories of the measurement means exhibiting the given spatial distribution S, and where $m_j$ are the positions of the points of the mesh in the observation zone.

Thus, an advantage afforded by the transfer function is to weight the values $V_i$ taking account of the relative positions $s_i$ and $m_j$, for example according to a distance or an angle arising from the relative positions $s_i$ and $m_j$.

According to an embodiment of the invention, the calculation means are configured to calculate the estimator of the set V according to the formula:

$$\hat{V}_j = \frac{\sum_{i=1}^{N} V_i [d(m_j, s_i)]^{-2}}{\sum_{i=1}^{N} [d(m_j, s_i)]^{-2}}, j \in [\![1, G]\!]$$

$m_j$ are the positions of the points of the mesh in the observation zone,
$s_i$ are the positions or the trajectories of the measurement means exhibiting the given spatial distribution S,
$V_i$ are the modeled values of the set V, which are extracted for the positions or for the trajectories $s_i$, and
d is a distance between a position of a point of the mesh and a position or a trajectory of the measurement means in the observation zone.

Thus, an advantage afforded by such an estimator is its simplicity of implementation for the calculations.

According to an embodiment of the present disclosure, the cost function is representative of the difference between $\hat{V}$ and $\overline{V}$, and the cost function is a norm of the difference between $\hat{V}$ and $\overline{V}$.

Thus, the minimization of such a cost function makes it possible to envisage the obtaining of a spatial distribution $S_{opt}$ best reflecting the quality of the air in the observation zone with reference to the modeled values.

According to an embodiment of the present disclosure, the cost function is representative of the difference between $\hat{V}$ and $\overline{V}$, and the calculation means are configured to calculate the cost function according to the formula:

$$\varphi(S) = \frac{1}{G} \sum_{j=1}^{G} (\hat{V}_j - \overline{V}_j)^2$$

where $\overline{V}_j$ are the modeled values of the set V, which are extracted for the points of the mesh.

According to an embodiment of the present disclosure, the cost function is representative of the difference between $\hat{V}$ and $\overline{V}$, and in which the calculation means are configured to perform a random modification of the given spatial distribution S according to a probability, denoted $p_{ji}$, satisfying:

$$p_{ji} = 1 \text{ if } \varphi(S^{(j)}) \leq \varphi(S^{(i)})$$
$$p_{ji} = \exp\left(\frac{\varphi(S^{(i)}) - \varphi(S^{(j)})}{c}\right) \text{ if } \varphi(S^{(j)}) > \varphi(S^{(i)})$$

where:
$S^{(i)}$ is an initial given spatial distribution,
$S^{(j)}$ is a given spatial distribution randomly modified,
c is a parameter; and
the calculation means are configured to iterate the random modification of the given spatial distribution S until the extraction of $S_{opt}$.

Thus, an advantage afforded is to obtain a robust algorithm with regard to the choice of the initial given spatial distribution, that is to say that the spatial distribution $S_{opt}$ does not depend on the initial given spatial distribution.

According to an embodiment of the present disclosure, the cost function is representative of the likelihood between $\hat{V}$ and $\overline{V}$, and the cost function comprises a scalar product of $\hat{V}$ and $\overline{V}$, preferably normalized.

Thus, the maximization of such a cost function makes it possible to envisage the obtaining of a spatial distribution $S_{opt}$ best reflecting the quality of the air in the observation zone with reference to the modeled values.

According to an embodiment of the present disclosure, the cost function is representative of the likelihood between $\hat{V}$ and $\overline{V}$, and in which the calculation means are configured to perform a random modification of the given spatial distribution S according to a probability, denoted $p_{ji}$, satisfying:

$$p_{ji} = 1 \text{ if } \varphi(S^{(j)}) \geq \varphi(S^{(i)})$$
$$p_{ji} = \exp\left(\frac{\varphi(S^{(j)}) - \varphi(S^{(i)})}{c}\right) \text{ if } \varphi(S^{(j)}) < \varphi(S^{(i)})$$

where:
$S^{(i)}$ is an initial given spatial distribution,
$S^{(j)}$ is a given spatial distribution randomly modified,
c is a parameter; and
the calculation means are configured to iterate the random modification of the given spatial distribution S until the extraction of $S_{opt}$.

Thus, an advantage afforded is to obtain a robust algorithm with regard to the choice of the initial given spatial distribution, that is to say that the spatial distribution $S_{opt}$ does not depend on the initial given spatial distribution.

According to an embodiment of the present disclosure, the measurement means are arranged in the observation zone in such a way as to possess N positions or N trajectories exhibiting the spatial distribution $S_{opt}$.

According to an embodiment of the present disclosure, the measurement system comprises activation means configured to activate the measurement means possessing N positions or N trajectories exhibiting the spatial distribution, which is closest to $S_{opt}$.

Thus, an advantage afforded is to optimize the electrical consumption of the measurement means when the latter comprise a total number $N_{tot}$ of positions or of trajectories in the observation zone satisfying $N_{tot} > N$. Indeed, it is then possible to deactivate the measurement means whose positions or trajectories in the observation zone do not belong to the N positions or N trajectories exhibiting the spatial distribution, which is closest to $S_{opt}$.

According to an embodiment of the present disclosure, the observation zone comprises a number M of permitted positions or a number M of permitted trajectories, satisfying $M > N$, in which the measurement means are respectively permitted to possess positions or trajectories.

According to an embodiment of the present disclosure, the measurement means comprise at least N measurement devices each fitted to a vehicle, the vehicle preferably being a road vehicle or aerial vehicle.

Thus, an advantage afforded is to be able to use the circulation of vehicles in the observation zone as deployment of measurement devices according to various spatial distributions of positions or of trajectories.

According to an embodiment of the present disclosure, the measurement means comprise at least N measurement devices each fitted to an item of urban furniture, the urban furniture preferably being selected from the group comprising traffic lights and bus shelters.

Thus, an advantage afforded is to avoid creating dedicated locations for the measurement devices.

According to an embodiment of the present disclosure, the measurement means comprise spectroscopic sensors, preferably non-dispersive infrared sensors.

Thus, an advantage afforded is their compactness with respect to conventional measurement stations, allowing a higher spatial density at lesser cost.

The subject of the present disclosure is also a method for measuring at least one physical quantity representative of the quality of the air in an observation zone, the method comprising the steps:
a) provide a mapping of the observation zone, comprising a set, denoted V, of modeled values representative of the physical quantity;
b) provide means for measuring the physical quantity, possessing a number N of positions or a number N of trajectories in the observation zone, the N positions or the N trajectories being intended to exhibit a spatial distribution, denoted $S_{opt}$;
c) construct a mesh of the observation zone, the mesh comprising a number G of points;
d) calculate, for a given spatial distribution, denoted S, of the N positions or of the N trajectories, an estimator of the set V, denoted $\hat{V}$, for each of the G points of the mesh;
e) calculate a cost function, denoted $\varphi(S)$, representative of the difference or of the likelihood between V and the modeled values of the set V, which are extracted at the G points of the mesh, denoted $\overline{V}$;
f) extract the spatial distribution $S_{opt}$, which minimizes or maximizes the cost function depending on whether the cost function is representative of the difference or of the likelihood between $\hat{V}$ and $\overline{V}$; and
g) arrange the measurement means in the observation zone so that the N positions or the N trajectories exhibit the spatial distribution $S_{opt}$.

BRIEF DESCRIPTION OF THE DRAWINGS

Other embodiments and advantages will become apparent in the detailed disclosure of various embodiments of the present disclosure, the disclosure being supplemented with examples and with reference to the attached drawings.

DETAILED DESCRIPTION

Figure 1:
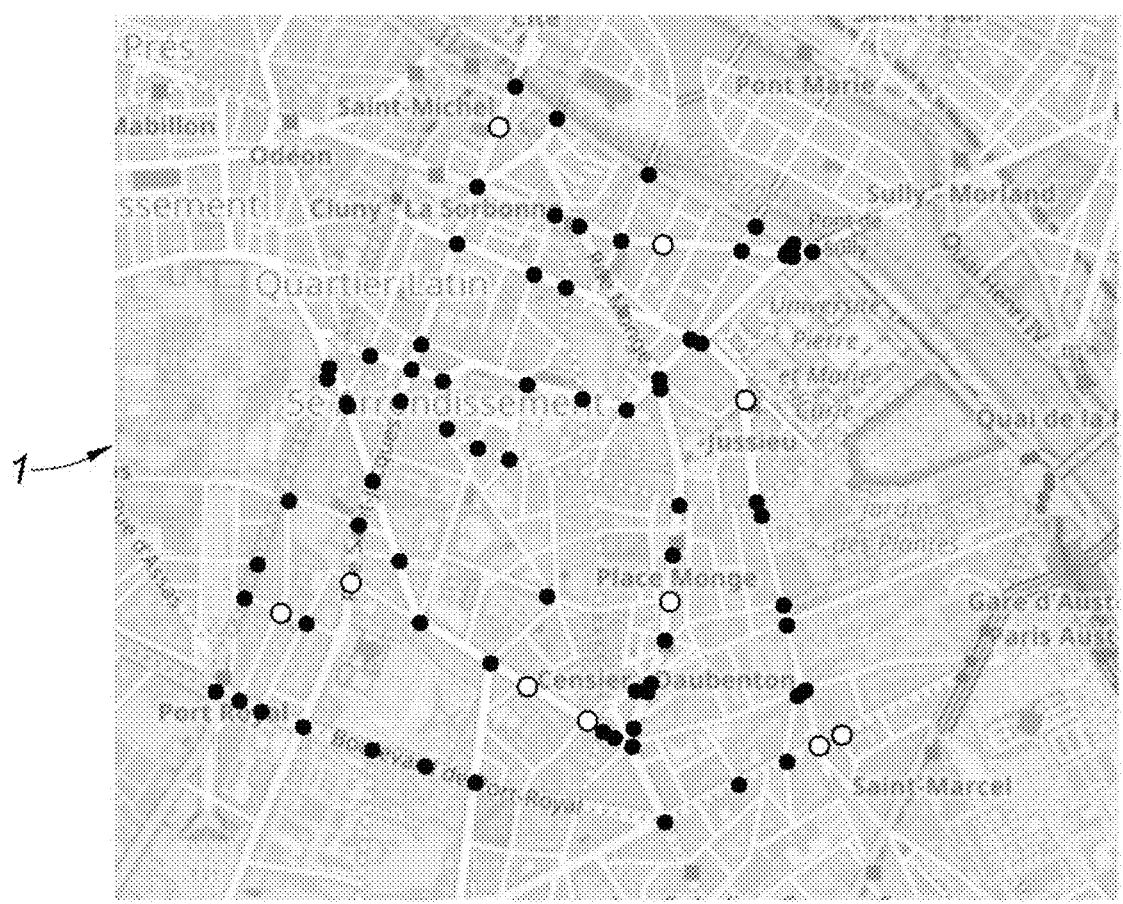
FIG. 1 is a partial schematic view of a measurement system according to the present disclosure, illustrating measurement means, arranged in an observation zone (a district of the city of Paris), and possessing N positions exhibiting the spatial distribution $S_{opt}$ (white dots, N=10), selected from among M permitted positions (black dots).
Figure 2:
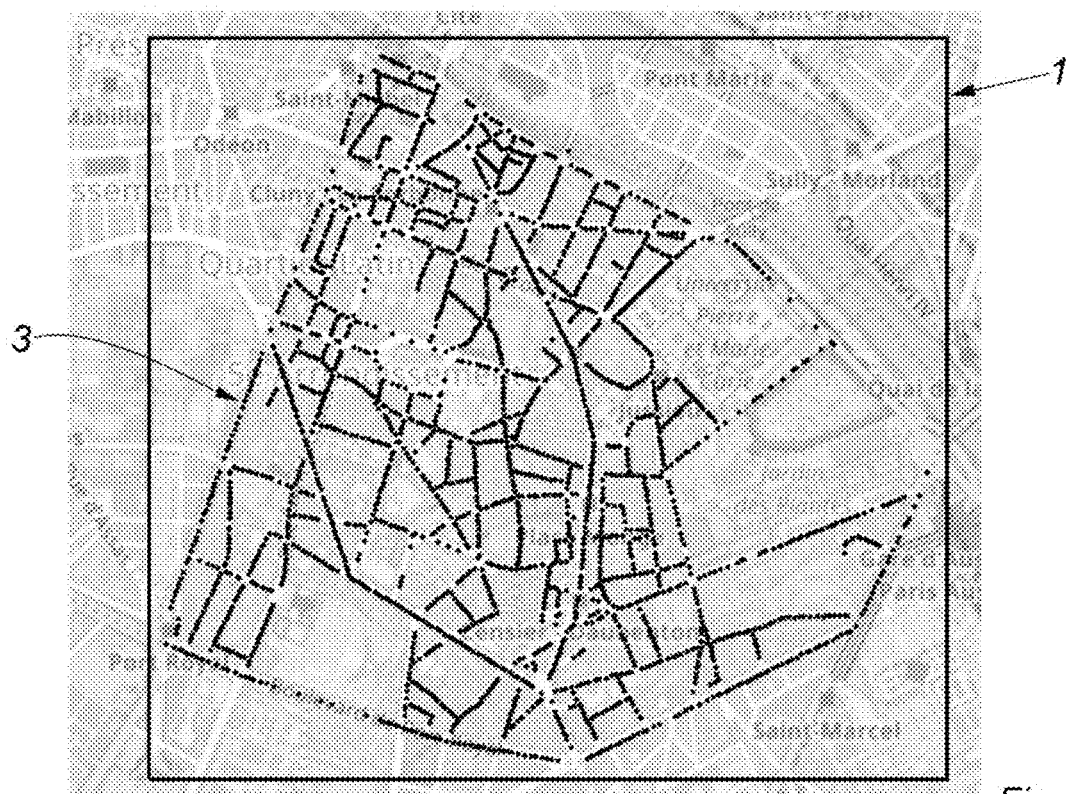
FIG. 2 is a partial schematic view of a measurement system according to the present disclosure, illustrating a mesh of an observation zone (a district of the city of Paris).
Figure 3:
FIG. 3 is a partial schematic view of a measurement system according to the present disclosure, illustrating a mapping of an observation zone (a district of the city of Paris), the mapping comprising a set of modeled values representative of the physical quantity to be measured.

Elements that are identical or that ensure the same function will bear the same references for the various embodiments, for the sake of simplification.

A subject of the present disclosure is a system for measuring at least one physical quantity representative of the quality of the air in an observation zone 1, the system comprising:
a mapping 2 of the observation zone 1, comprising a set, denoted V, of modeled values representative of the physical quantity;
means for measuring the physical quantity, possessing a number N of positions or a number N of trajectories in the observation zone 1, the N positions or the N trajectories being intended to exhibit a spatial distribution, denoted $S_{opt}$, in the observation zone 1; and
means for calculating the spatial distribution $S_{opt}$, configured to:

construct a mesh 3 of the observation zone 1, the mesh 3 comprising a number G of points;

calculate, for a given spatial distribution, denoted S, of the N positions or of the N trajectories, an estimator of the set V, denoted $\hat{V}$, for each of the G points of the mesh 3;

calculate a cost function, denoted φ(S), representative of the difference or of the likelihood between $\hat{V}$ and the modeled values, denoted $\overline{V}$, of the set V, which are extracted at the G points of the mesh 3; and extract the spatial distribution $S_{opt}$, which minimizes or maximizes the cost function depending on whether the cost function is representative of the difference or of the likelihood between $\hat{V}$ and $\overline{V}$.

Physical Quantity:

By way of nonlimiting examples, the physical quantity or quantities may be concentrations of polluting molecules or concentrations of noxious particles that are harmful to the environment. It is possible to cite carbon monoxide CO, sulfur dioxide $SO_2$, nitrogen dioxide $NO_2$, particulate matter in suspension (SPM for "Suspended Particulate Matter"), respirable particulate matter in suspension (RSPM for "Respirable Suspended Particulate Matter"), polycyclic aromatic hydrocarbons (PAHs), and/or ozone $O_3$.

Observation Zone:

By way of nonlimiting examples, the observation zone 1 may be an urban zone, a peri-urban zone, an industrial zone.

The observation zone 1 may comprise a number M of permitted positions or a number M of permitted trajectories, satisfying M>N, in which the measurement means are respectively permitted to possess positions or trajectories. M is a natural integer.

Mapping:

There exist in the prior art mappings 2 of observation zones 1, generally urban, that can comprise modeled values of the spatial distribution of concentrations in polluting molecules or in noxious particles. These mappings 2 arise conventionally from models developed for studying atmospheric pollution and its temporal evolution. By way of nonlimiting example, the publication by R. Berkowicz et al., "*Modeling traffic pollution in streets*", National Environmental Research Institute, dated January 1997, describes a model of spatial dispersion of pollutants that is adapted to suit the specific features of urban zones. In an urban setting, the particular topography formed of streets separated by buildings justifies a specific approach, taking account of the formation of air circulation vortices in the streets, these vortices playing a determining role in the dispersion of atmospheric pollution. Such models are referred to by the terms "Street Canyon Model" or "Street Model". The aforementioned publication describes a model for estimating pollution in an urban setting referred to by the acronym OSPM ("Operational Street Pollution Model"), that is to say an operational urban pollution model. According to this model, on the basis of the emission of a pollutant in a street, depending on the number of vehicles and an average emission per vehicle, the model takes into account the recirculation vortex formed in the street, the aerological turbulence resulting from road traffic, the ambient pollution, originating from other streets, as well as the wind circulating in the canopy, above the urban setting. The publication by R. Berkowicz "*OSPM—A Parameterised Street Pollution Model*", Environmental Monitoring and Assessment, 65(1), pp. 323-331, 2000, also presents the assumptions on which the OSPM model is based, as well as an experimental validation of this model.

The mapping 2 of the set V of modeled values can represent the measured physical quantity directly. According to a variant, the mapping 2 of the set V of modeled values can represent the measured physical quantity indirectly, by correlation. By way of nonlimiting examples, it is possible to cite values that model sound nuisance, sunshine, wind, temperature, road traffic, electromagnetic waves (radio, mobile telephone).

The mapping 2 exhibits a greater spatial resolution than that of the mesh 3.

Means for Measuring the Physical Quantity:

The measurement means comprise measurement devices. The measurement devices advantageously comprise spectroscopic sensors, preferably non-dispersive infrared sensors.

According to one embodiment, the measurement means are arranged in the observation zone 1 in such a way as to possess N positions or N trajectories exhibiting the spatial distribution $S_{opt}$. According to a variant, the measurement system comprises activation means configured to activate the measurement means possessing N positions or N trajectories exhibiting the spatial distribution that is closest to $S_{opt}$. By way of example, the activation means can be controlled from a central regulating post.

According to one embodiment, the measurement means comprise at least N measurement devices each fitted to a vehicle, the vehicle preferably being a road vehicle or aerial vehicle. By way of nonlimiting examples, the road vehicle may be a car or a bus; the aerial vehicle may be a pilotless aircraft such as a drone. According to a variant, the measurement means comprise at least N measurement devices each fitted to an item of urban furniture, the urban furniture preferably being selected from the group comprising traffic lights and bus shelters.

Example No. 1

Figure 9:
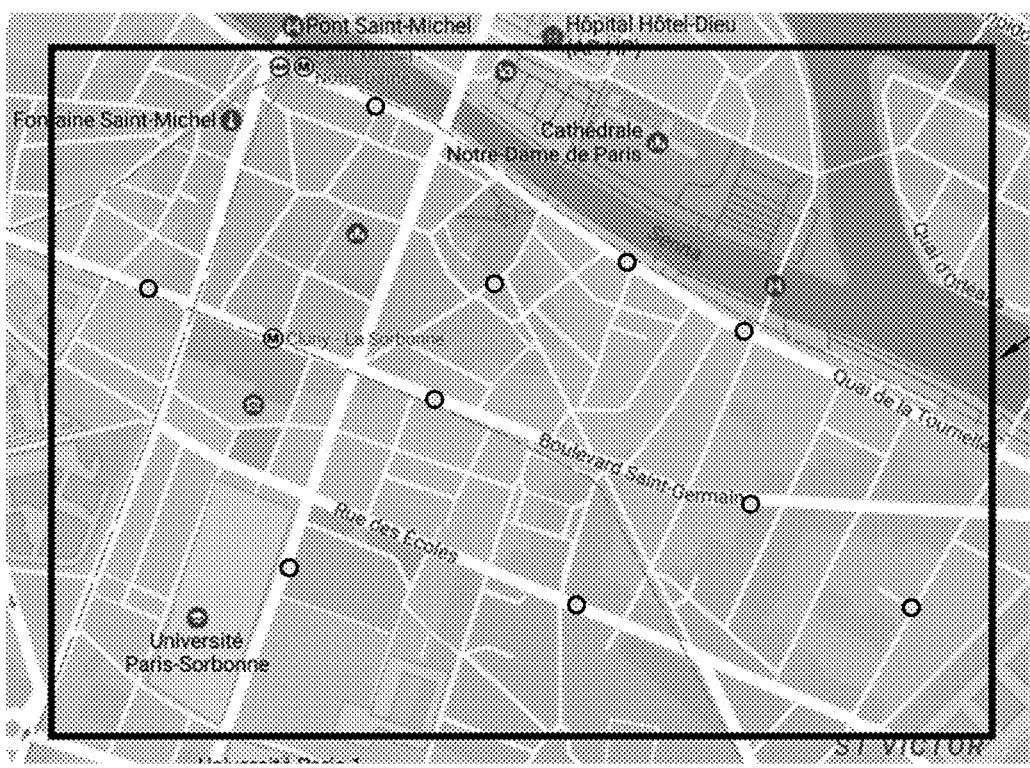
FIG. 9 is a partial schematic view of a measurement system according to the present disclosure, illustrating measurement means, arranged in an observation zone (a district of the city of Paris), and possessing N positions exhibiting the spatial distribution $S_{opt}$ (white dots, N=10).

In this example illustrated in FIG. 9, the measurement means comprise N fixed measurement devices in the observation zone 1. The N measurement devices are arranged in the observation zone 1 so as to possess N positions exhibiting the spatial distribution $S_{opt}$ (white dots).

Example No. 2

Figure 10:
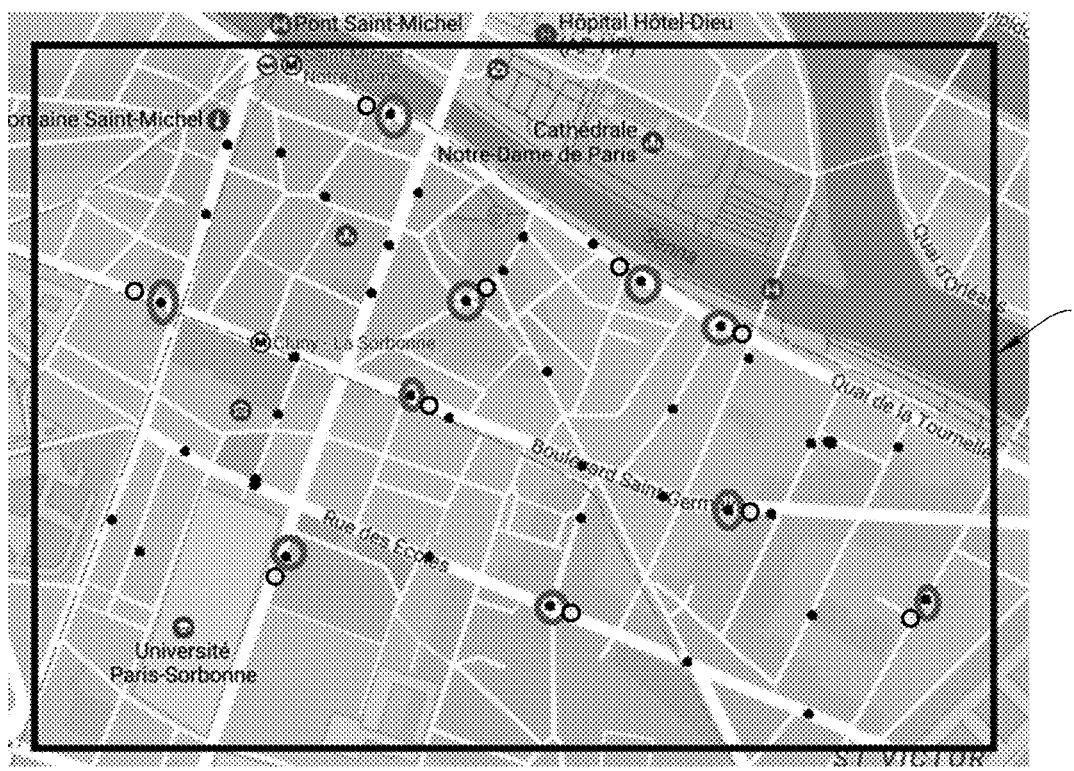
FIG. 10 is a partial schematic view of a measurement system according to the present disclosure, comprising activation means configured to activate fixed measurement means in the observation zone, and possessing N positions exhibiting the spatial distribution, which is closest to $S_{opt}$ (encircled black dots, N=10). The spatial distribution $S_{opt}$ extracted is illustrated by white dots. The set of fixed positions of the measurement means is illustrated by black dots.

In this example illustrated in FIG. 10, the measurement means comprise a total number $N_{tot}$ of fixed measurement devices ($N_{tot}$>N, black dots) in the observation zone 1. The measurement system comprises activation means configured to activate, over a given period, the measurement devices possessing N positions exhibiting the spatial distribution that is closest to $S_{opt}$ (encircled black dots). The spatial distribution $S_{opt}$ extracted is illustrated by white dots.

Example No. 3

Figure 11:
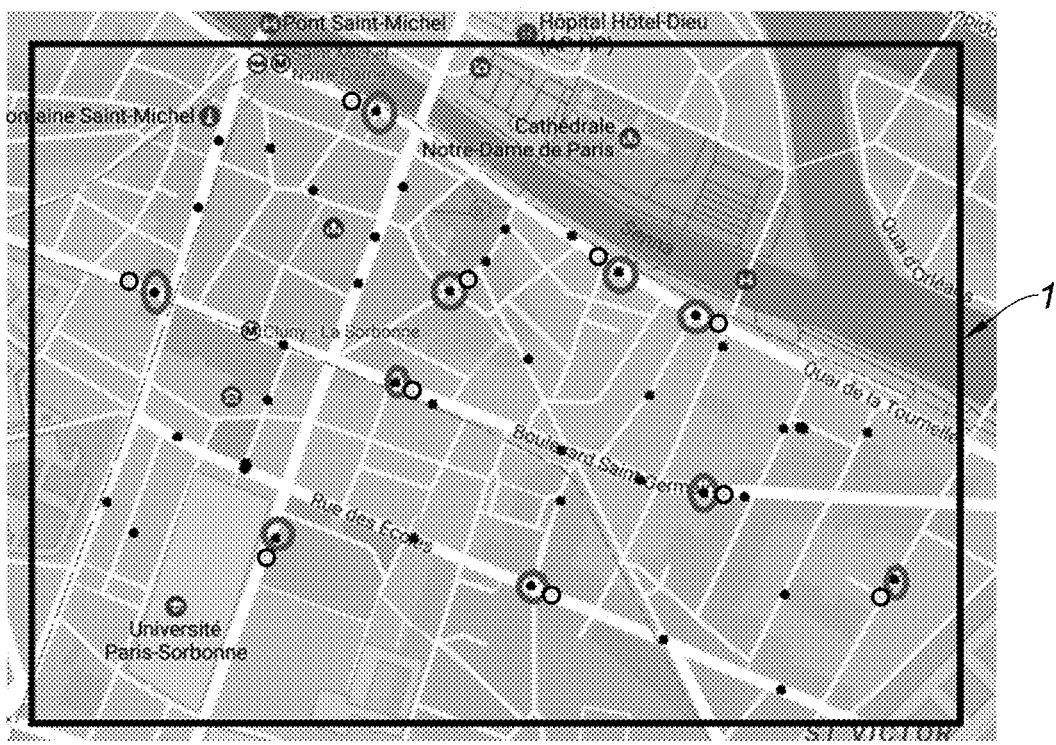
FIG. 11 is a partial schematic view of a measurement system according to the present disclosure, comprising activation means configured to activate mobile measurement means in the observation zone, and possessing N positions, at a given instant, exhibiting the spatial distribution, which is closest to $S_{opt}$ (encircled black dots, N=10). The spatial distribution $S_{opt}$ extracted is illustrated by white dots. The set of positions of the measurement means, at a given instant, is illustrated by black dots.

In this example illustrated in FIG. 11, the measurement means comprise a total number $N_{tot}$ of mobile measurement devices ($N_{tot}$>N, black dots) in the observation zone 1. The measurement system comprises activation means configured to activate, at given instant, the measurement devices possessing N positions exhibiting the spatial distribution that is closest to $S_{opt}$ (encircled black dots). The spatial distribution $S_{opt}$ extracted is illustrated by white dots.

Example No. 4

Figure 12:
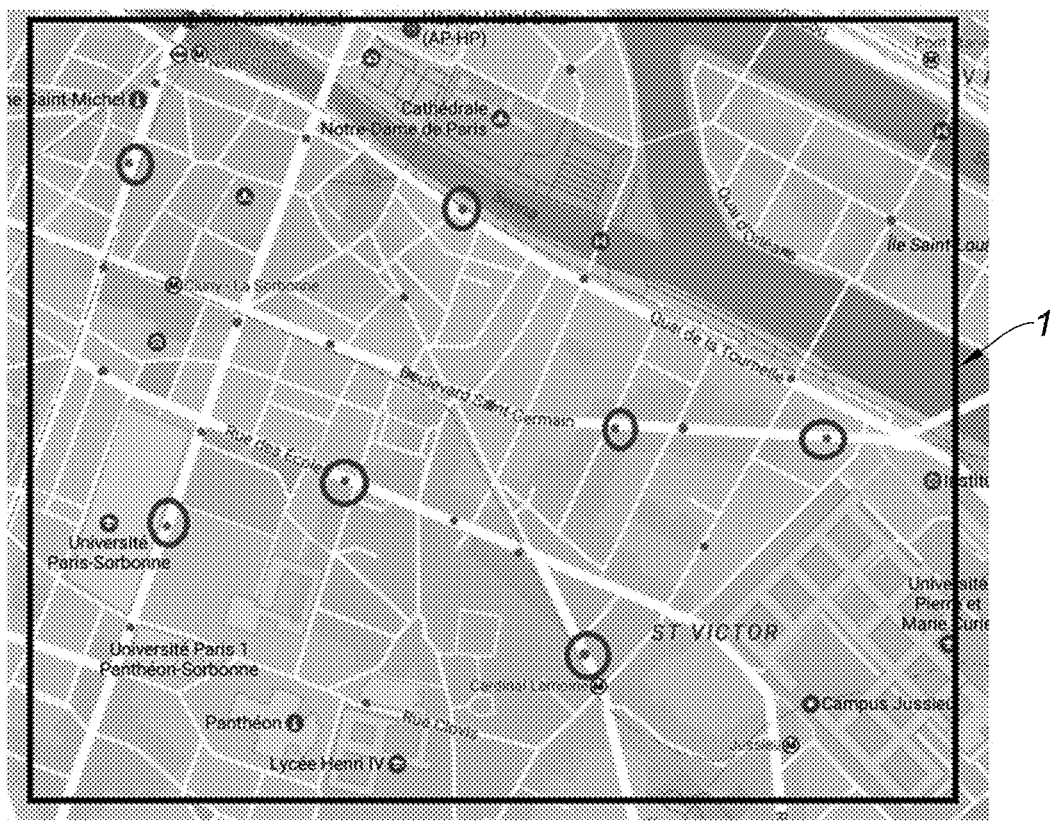
FIG. 12 is a partial schematic view of a measurement system according to the present disclosure, illustrating measurement means, arranged in an observation zone, and possessing N positions exhibiting the spatial distribution $S_{opt}$ (encircled points, N=7), selected from among M permitted positions (points).

In this example illustrated in FIG. 12, the observation zone 1 comprises M permitted positions (points). The measurement means comprise N measurement devices arranged in the observation zone 1 in such a way as to possess N positions (from among the M permitted positions) exhibiting the spatial distribution $S_{opt}$ (encircled points).

Example No. 5

Figure 13:
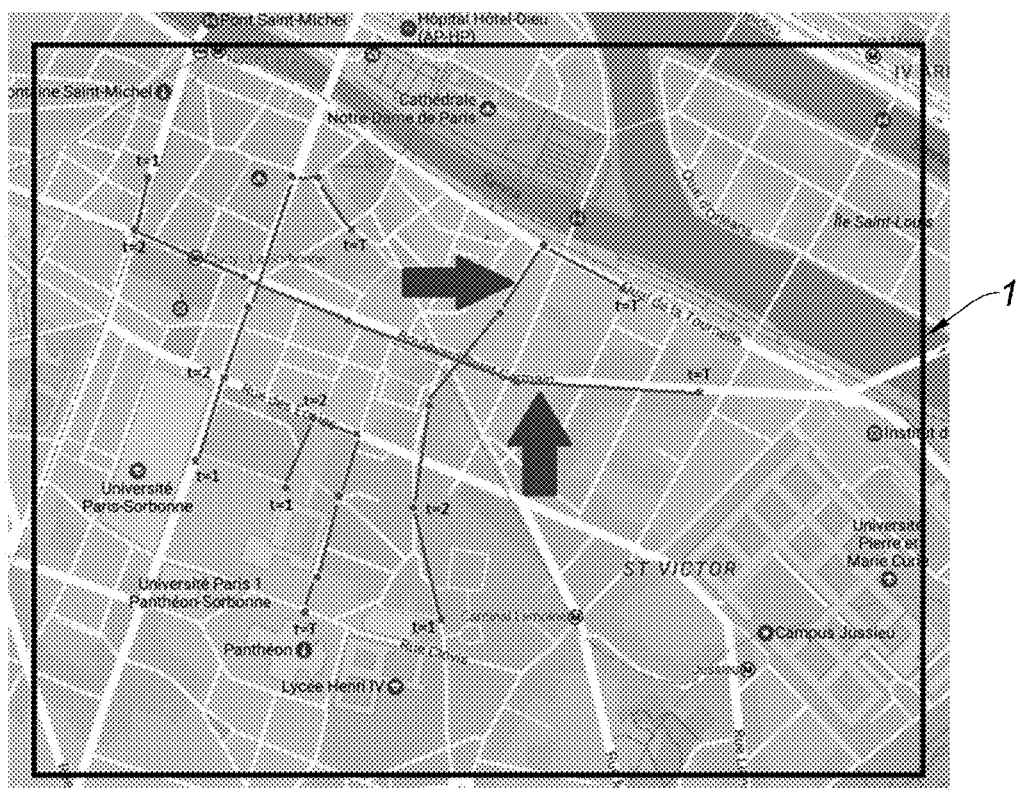
FIG. 13 is a partial schematic view of a measurement system according to the present disclosure, illustrating measurement means, arranged in an observation zone, and possessing N trajectories (pointed at by the arrows, N=2) exhibiting the spatial distribution $S_{opt}$, which are selected from among M permitted trajectories (M=4).

In this example illustrated in FIG. 13, the observation zone 1 comprises M permitted trajectories. The measurement means comprise N measurement devices arranged in the observation zone 1 so as to possess N trajectories (from among the M permitted trajectories) exhibiting the spatial distribution $S_{opt}$ (which are pointed at by the arrows).

Means for Calculating the Spatial Distribution $S_{Opt}$:

The calculation means are advantageously implemented by computer or by any programmable device comprising the suitable calculation instructions.

Estimator of the Set V:

The calculation means are advantageously configured to calculate the estimator of the set V according to the formula:

$$\hat{V}_j = \frac{\sum_{i=1}^{N} V_i w_{ij}}{\sum_{i=1}^{N} w_{ij}}, j \in [\![1, G]\!]$$

where:

$V_i$ are the modeled values of the set V, which are extracted for the positions or for the trajectories of the measurement means exhibiting the given spatial distribution S, and $w_{ij}$ is a transfer function going between $s_i$ and $m_j$, where $s_i$ are the positions or the trajectories of the measurement means exhibiting the given spatial distribution S, and where $m_j$ are the positions of the points of the mesh 3 in the observation zone 1.

The transfer function makes it possible to weight the values V, taking account of the relative positions $s_i$ and $m_j$, for example, according to a distance or an angle arising from the relative positions $s_i$ and $m_j$.

The calculation means are advantageously configured to calculate the estimator of the set V according to the formula:

$$\hat{V}_j = \frac{\sum_{i=1}^{N} V_i [d(m_j, s_i)]^{-2}}{\sum_{i=1}^{N} [d(m_j, s_i)]^{-2}}, j \in [\![1, G]\!]$$

where:

$m_j$ are the positions of the points of the mesh in the observation zone, $s_i$ are the positions or the trajectories of the measurement means exhibiting the given spatial distribution S, $V_i$ are the modeled values of the set V, which are extracted for the positions or for the trajectories $s_i$, and d is a distance between a position of a point of the mesh 3 and a position or a trajectory of the measurement means in the observation zone 1.

The distance d can be a road distance or a Euclidean distance (i.e., as the crow flies).

Cost Function:

When the cost function is representative of the difference between $\hat{V}$ and $\overline{V}$, the cost function is advantageously a norm of the difference between $\hat{V}$ and $\overline{V}$. When the cost function is representative of the difference between $\hat{V}$ and $\overline{V}$, the calculation means are advantageously configured to calculate the cost function according to the formula:

$$\varphi(S) = \frac{1}{G} \sum_{j=1}^{G} (\hat{V}_j - \overline{V}_j)^2$$

where $\overline{V}_j$ are the modeled values of the set V, which are extracted for the points of the mesh 3.

When the cost function is representative of the likelihood between $\hat{V}$ and $\overline{V}$, the cost function advantageously comprises a scalar product of $\hat{V}$ and $\overline{V}$, preferably normalized.

Algorithm for Extracting $S_{Opt}$:

When the cost function is representative of the difference between $\hat{V}$ and $\overline{V}$, the calculation means are advantageously configured to perform a random modification of the given spatial distribution S according to a probability, denoted $p_{ji}$, satisfying:

$$p_{ji} = 1 \text{ if } \varphi(S^{(j)}) \leq \varphi(S^{(i)})$$
$$p_{ji} = \exp\left(\frac{\varphi(S^{(i)}) - \varphi(S^{(j)})}{c}\right) \text{ if } \varphi(S^{(j)}) > \varphi(S^{(i)})$$

where:

$S^{(i)}$ is an initial given spatial distribution, $S^{(j)}$ is a given spatial distribution randomly modified, and c is a parameter.

If one considers an iteration, denoted t, the parameter c is preferably chosen so that: $c(t+1) = \alpha c(t); \alpha \approx 1$.

The calculation means are configured to iterate the random modification of the given spatial distribution S until the extraction of $S_{opt}$. The calculation means are configured to apply a stopping criterion to the iterations. By way of example, the stopping criterion may be defined when the difference $|\varphi(S^{(j+1)}) - \varphi(S^{(j)})|$ is less than a predetermined threshold.

When the cost function is representative of the likelihood between $\hat{V}$ and $\overline{V}$, the calculation means are advantageously configured to perform a random modification of the given spatial distribution S according to a probability, denoted $p_{ji}$, satisfying:

$$p_{ji} = 1 \text{ if } \varphi(S^{(j)}) \geq \varphi(S^{(i)})$$
$$p_{ji} = \exp\left(\frac{\varphi(S^{(j)}) - \varphi(S^{(i)})}{c}\right) \text{ if } \varphi(S^{(j)}) < \varphi(S^{(i)})$$

where:

$S^{(i)}$ is an initial given spatial distribution, $S^{(j)}$ is a given spatial distribution randomly modified, and c is a parameter.

If one considers an iteration, denoted t, the parameter c is preferably chosen so that: $c(t+1) = \alpha c(t); \alpha \approx 1$.

The calculation means are configured to iterate the random modification of the given spatial distribution S until the extraction of $S_{opt}$. The calculation means are configured to apply a stopping criterion to the iterations. By way of example, the stopping criterion may be defined when the difference $|\varphi(S^{(j+1)}) - \varphi(S^{(j)})|$ is less than a predetermined threshold.

Figure 4:
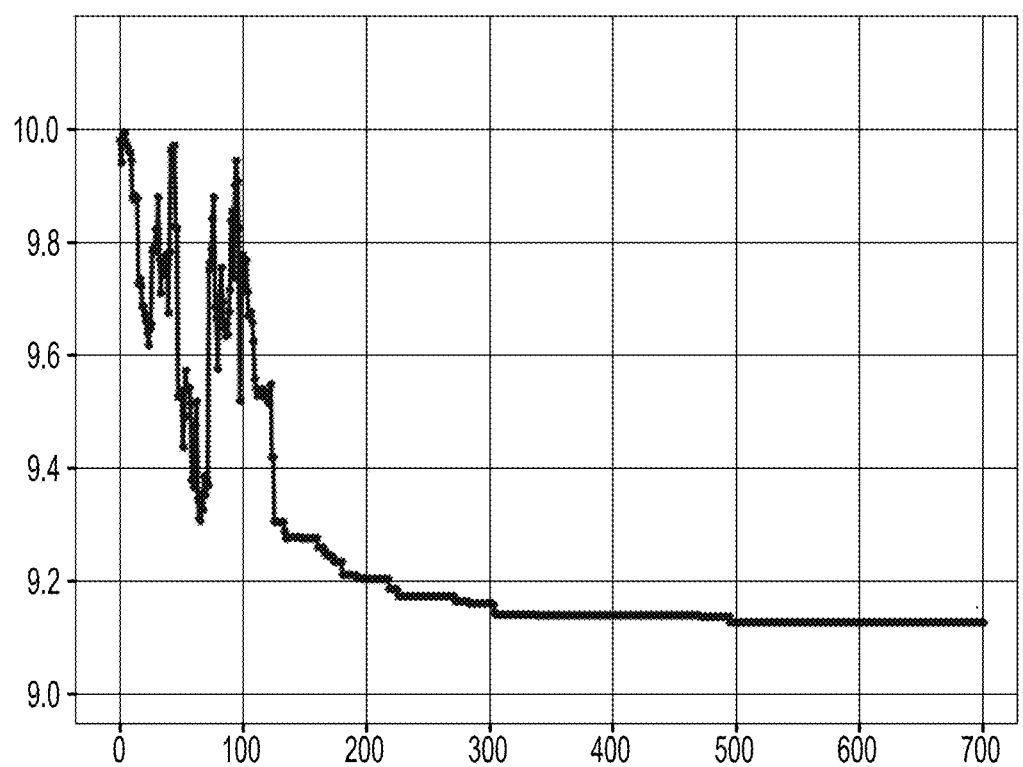
FIG. 4 is a graph illustrating as ordinate the cost function and as abscissa the number of iterations (i.e., the number of modifications of the spatial distribution of the N positions or N trajectories).
Figure 5:
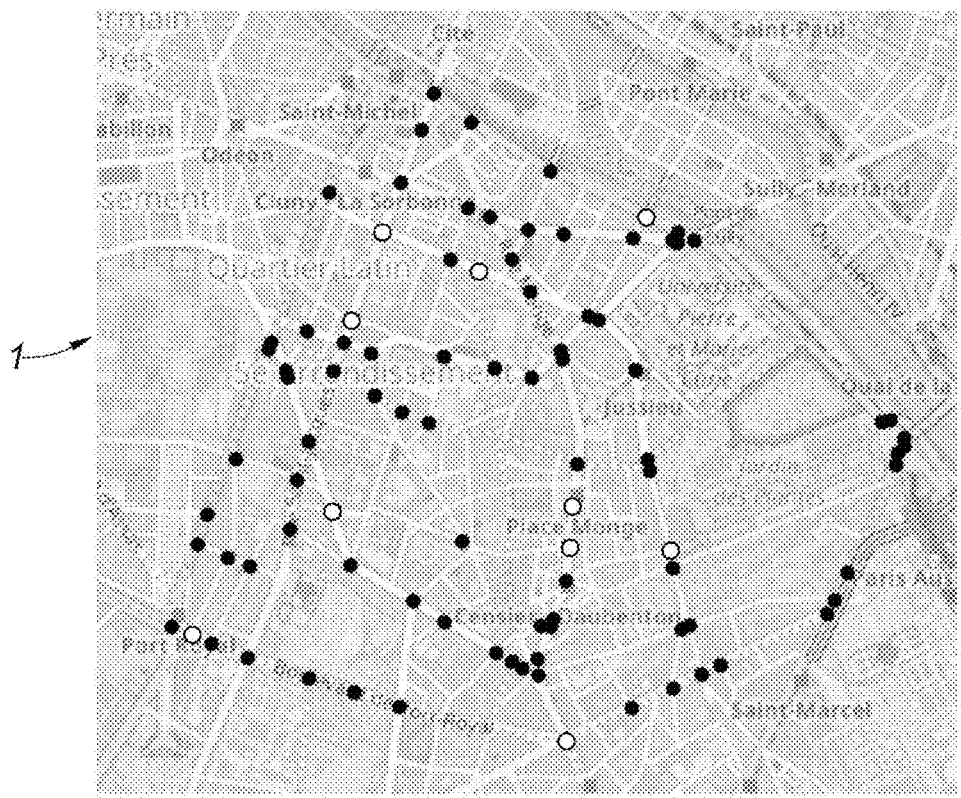
FIGS. 5 to 7 are views analogous to FIG. 1, illustrating respectively an initial spatial distribution (white dots) of the N positions (N=10), an intermediate spatial distribution (white dots) of the N positions, and the spatial distribution $S_{opt}$ (white dots) of the N positions, selected from among M permitted positions (black dots).
Figure 6:
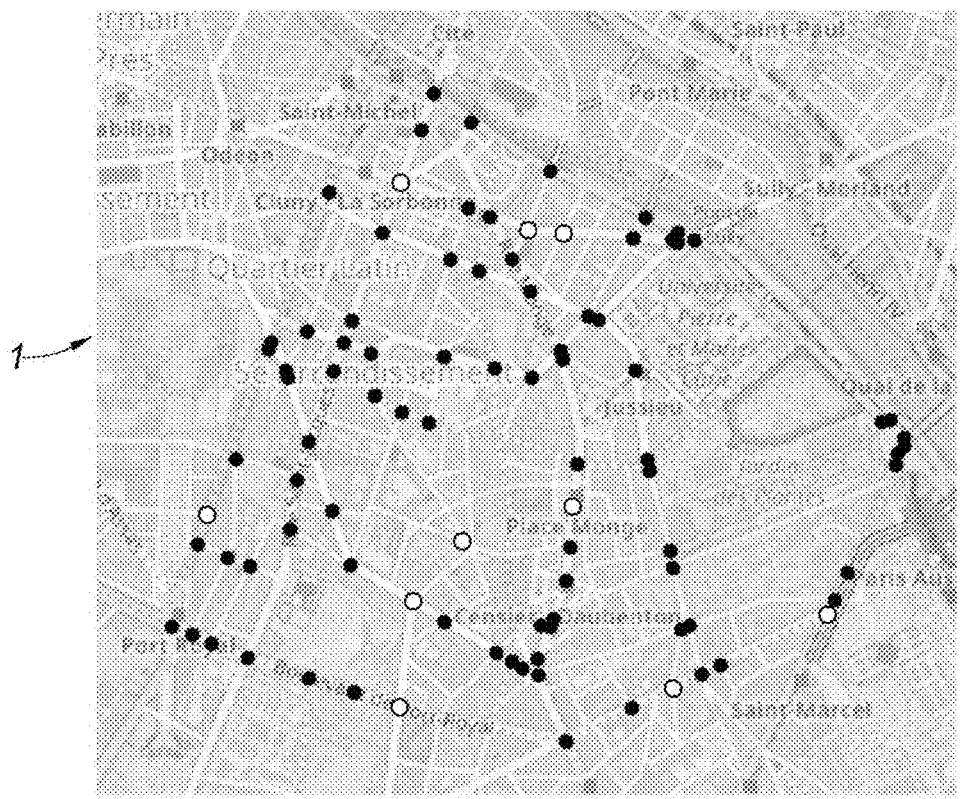
Figure 7:
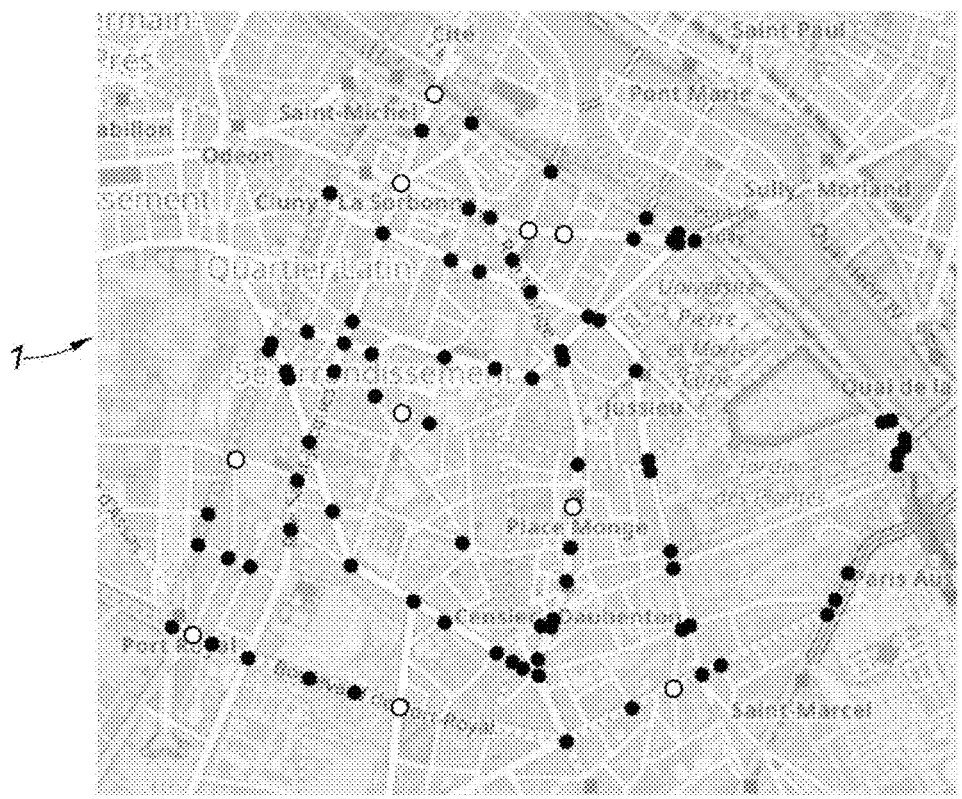
Figure 8:
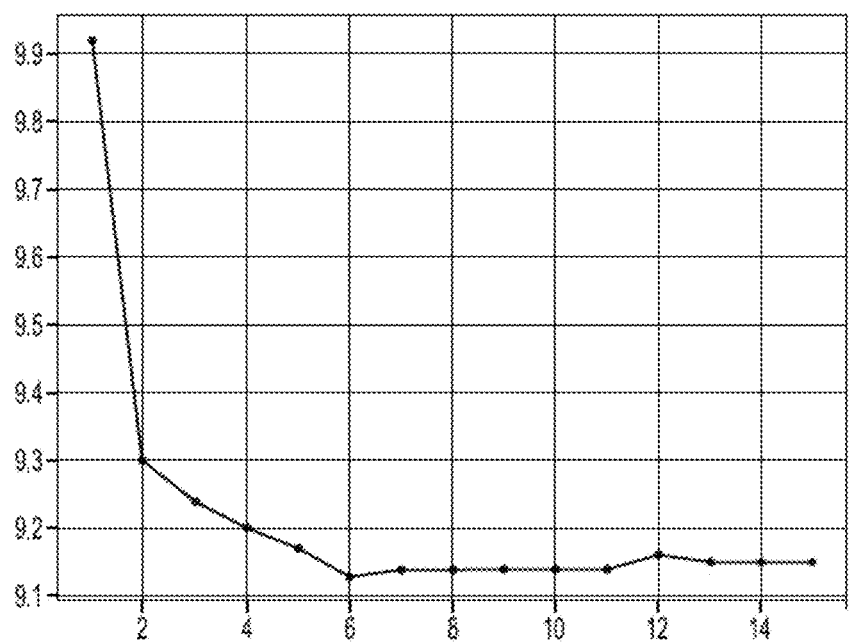
FIG. 8 is a graph illustrating as ordinate the cost function and as abscissa the number N of positions or of trajectories.

As illustrated in FIG. 4, such an algorithm converges after a certain number of iterations. As illustrated in FIG. 8, it is also possible to vary the number N of positions or of trajectories so as to determine the spatial distribution $S_{opt}$ with the minimum number N (N=6 in FIG. 6) making it possible to minimize or maximize the cost function depending on whether the cost function is representative of the difference or of the likelihood between $\hat{V}$ and $\overline{V}$.

The algorithm operates in an analogous manner with N positions or N trajectories of the measurement means. In the case where the measurement means possess N trajectories in the observation zone 1, the successive positions of the N trajectories are sampled at T instants. $\hat{V}$ and $\overline{V}$ are then vectors comprising T elements. In the case where the measurement means possess N positions in the observation zone 1, $\hat{V}$ and $\overline{V}$ are scalars.

The present disclosure is not limited to the embodiments set forth. The person skilled in the art is at liberty to consider their technically operative combinations, and to substitute equivalents for them.

The invention claimed is:

1. A system for measuring at least one physical quantity representative of air quality in an observation zone, the system comprising:
   a mapping of the observation zone, comprising a set, denoted V, of modeled values representative of the at least one physical quantity;
   measuring devices configured to measure the at least one physical quantity, possessing a total number $N_{tot}$ of positions or a total number $N_{tot}$ of trajectories in the observation zone, the $N_{tot}$ positions or the $N_{tot}$ trajectories exhibiting a spatial distribution in the observation zone;
   a calculator of a spatial distribution, denoted $S_{opt}$, of a subset of the measuring devices possessing a number N of positions or a number N of trajectories in the observation zone, the calculator configured to:
     construct a mesh of the observation zone, the mesh comprising a number G of points;
     calculate, for a given spatial distribution, denoted S, of the N positions or of the N trajectories, an estimator of the set V, denoted $\hat{V}$, for each of the G points of the mesh;
     calculate a cost function, denoted $\varphi(S)$, representative of a difference or of a likelihood between $\hat{V}$ and the modeled values, denoted $\overline{V}$, of the set V extracted at the G points of the mesh; and
     extract the spatial distribution $S_{opt}$ to minimize or maximize the cost function in dependence on whether the cost function is representative of the difference or of the likelihood between $\hat{V}$ and $\overline{V}$; and
   an activation means configured to:
     activate some of the measuring devices possessing N positions or N trajectories exhibiting a spatial distribution that is closest to the extracted spatial distribution $S_{opt}$; and
     deactivate others of the measuring devices possessing N positions or N trajectories exhibiting a spatial distribution that deviates from the extracted spatial distribution $S_{opt}$,
   each of the measuring devices being fitted to a vehicle or urban structure within the observation zone, and
   the measuring devices being arranged in the observation zone to at least partially satisfy the extracted spatial distribution $S_{opt}$ in order to measure the at least one physical quantity representative of air quality in the observation zone.

2. The system of claim 1, wherein the calculator of the spatial distribution $S_{opt}$ is configured to calculate the estimator of the set V according to the formula:

$$\hat{V}_j = \frac{\sum_{i=1}^{N} V_i w_{ij}}{\sum_{i=1}^{N} w_{ij}}, j \in [\![1, G]\!]$$

wherein:
   $V_i$, are the modeled values of the set V extracted for the positions or for the trajectories of the measuring devices configured to measure the at least one physical quantity and exhibiting the given spatial distribution S, and
   $w_{ij}$ is a transfer function going between $s_i$ and $m_j$, wherein $s_i$ are the positions or the trajectories of the measuring devices configured to measure the at least one physical quantity and exhibiting the given spatial distribution S, and wherein $m_j$ are the positions of the points of the mesh in the observation zone.

3. The system of claim 1, wherein the calculator of the spatial distribution $S_{opt}$ is configured to calculate the estimator of the set V according to the formula:

$$\hat{V}_j = \frac{\sum_{i=1}^{N} V_i [d(m_j, s_i)]^{-2}}{\sum_{i=1}^{N} [d(m_j, s_i)]^{-2}}, j \in [\![1, G]\!]$$

wherein:
   $m_j$ are the positions of the points of the mesh in the observation zone,
   $s_i$, are the positions or the trajectories of the measuring devices configured to measure the at least one physical quantity and exhibiting the given spatial distribution S,
   $V_i$ are the modeled values of the set V extracted for the positions or for the trajectories $s_i$, and
   d is a distance between a position of a point of the mesh and a position or a trajectory of the measuring devices in the observation zone.

4. The system of claim 1, wherein the cost function is representative of the difference between $\hat{V}$ and $\overline{V}$, and the cost function is a norm of the difference between $\hat{V}$ and $\overline{V}$.

5. The system of claim 1, wherein the cost function is representative of the difference between $\hat{V}$ and $\overline{V}$, and the calculator of the spatial distribution $S_{opt}$ is configured to calculate the cost function according to the formula:

$$\varphi(S) = \frac{1}{G} \sum_{j=1}^{G} (\hat{V}_j - \overline{V}_j)^2$$

wherein $\overline{V}_j$ are the modeled values of the set V extracted for the points of the mesh.

6. The system of claim 1, wherein:
   the cost function is representative of the difference between $\hat{V}$ and $\overline{V}$;
   the calculator of the spatial distribution $S_{opt}$ is configured to perform a random modification of the given spatial distribution S according to a probability, denoted $p_{ji}$, satisfying:

$$p_{ji} = 1 \text{ if } \varphi(S^{(j)}) \leq \varphi(S^{(i)})$$

$$p_{ji} = \exp\left(\frac{\varphi(S^{(i)}) - \varphi(S^{(j)})}{c}\right) \text{ if } \varphi(S^{(j)}) > \varphi(S^{(i)})$$

wherein:
$S^{(i)}$ is an initial given spatial distribution,
$S^{(j)}$ is a given spatial distribution randomly modified, and
c is a parameter; and
the calculator of the spatial distribution $S_{opt}$ is further configured to iterate the random modification of the given spatial distribution S until an extraction of $S_{opt}$.

7. The system of claim 1, wherein the cost function is representative of the likelihood between $\hat{V}$ and $\overline{V}$, and the cost function comprises a scalar product of $\hat{V}$ and $\overline{V}$.

8. The system of claim 1, wherein:
the cost function is representative of the likelihood between $\hat{V}$ and $\overline{V}$;
the calculator of the spatial distribution $S_{opt}$ is configured to perform a random modification of the given spatial distribution S according to a probability, denoted $p_{ji}$, satisfying:

$$p_{ji} = 1 \text{ if } \varphi(S^{(j)}) \geq \varphi(S^{(i)})$$

$$p_{ji} = \exp\left(\frac{\varphi(S^{(j)}) - \varphi(S^{(i)})}{c}\right) \text{ if } \varphi(S^{(j)}) < \varphi(S^{(i)})$$

wherein:
$S^{(i)}$ is an initial given spatial distribution,
$S^{(j)}$ is a given spatial distribution randomly modified, and
c is a parameter; and
the calculator of the spatial distribution $S_{opt}$ is further configured to iterate the random modification of the given spatial distribution S until an extraction of $S_{opt}$.

9. The system of claim 1, wherein the measuring devices configured to measure the at least one physical quantity are arranged in the observation zone in such a way as to possess the N positions or the N trajectories exhibiting the spatial distribution $S_{opt}$.

10. The system of claim 1, wherein the observation zone comprises a number M of permitted positions or a number M of permitted trajectories, satisfying M>N, wherein the measuring devices configured to measure the at least one physical quantity are respectively permitted to possess positions or trajectories.

11. The system of claim 1, wherein the measuring devices configured to measure the at least one physical quantity comprise at least N measuring devices each fitted to a vehicle.

12. The system of claim 1, wherein the measuring devices configured to measure the at least one physical quantity comprise at least N measuring devices each fitted to the urban structure within the observation zone, the urban structure comprising an item of urban furniture.

13. The system of claim 1, wherein the measuring devices configured to measure the at least one physical quantity comprise spectroscopic sensors.

14. The system of claim 7, wherein the scalar product of $\hat{V}$ and $\overline{V}$ is normalized.

15. The system of claim 11, wherein the vehicle is a road vehicle or an aerial vehicle.

16. The system of claim 12, wherein the item of urban furniture is selected from a group comprising traffic lights and bus shelters.

17. The system of claim 13, wherein the spectroscopic sensors comprises non-dispersive infrared sensors.

18. A method for measuring at least one physical quantity representative of air quality in an observation zone, the method comprising:
a) providing a mapping of the observation zone, the mapping comprising a set, denoted V, of modeled values representative of the at least one physical quantity;
b) providing measuring devices configured to measure the at least one physical quantity, possessing a total number $N_{tot}$ of positions or a total number $N_{tot}$ of trajectories in the observation zone, the $N_{tot}$ positions or the $N_{tot}$ trajectories exhibiting a spatial distribution in the observation zone;
c) constructing a mesh of the observation zone, the mesh comprising a number G of points;
d) calculating, for a given spatial distribution, denoted S, of the $N_{tot}$ positions or of the $N_{tot}$ trajectories, an estimator of the set V, denoted $\hat{V}$, for each of the G points of the mesh;
e) calculating a cost function, denoted $\varphi(S)$, representative of a difference or of a likelihood between $\hat{V}$ and the modeled values, denoted $\overline{V}$, of the set V extracted at the G points of the mesh;
f) extracting a spatial distribution, denoted $S_{opt}$, of a subset of the measuring devices possessing a number N of positions or a number N of trajectories in the observation zone, the spatial distribution $S_{opt}$ being extracted to minimize or maximize the cost function in dependence on whether the cost function is representative of the difference or of the likelihood between $\hat{V}$ and $\overline{V}$;
g) arranging, in the observation zone, the measuring devices configured to measure the at least one physical quantity so that the N positions or the N trajectories at least partially exhibit the spatial distribution $S_{opt}$, each of the measuring devices being fitted to a vehicle or an urban structure within the observation zone;
h) activating some of the measuring devices possessing N positions or N trajectories exhibiting a spatial distribution that is closest to the extracted spatial distribution $S_{opt}$; and
i) deactivating others of the measuring devices possessing N positions or N trajectories exhibiting a spatial distribution that deviates from the extracted spatial distribution $S_{opt}$.

* * * * *

UNITED STATES PATENT AND TRADEMARK OFFICE
CERTIFICATE OF CORRECTION

PATENT NO. : 11,408,877 B2
APPLICATION NO. : 16/606201
DATED : August 9, 2022
INVENTOR(S) : Paolo Zanini It is certified that error appears in the above-identified patent and that said Letters Patent is hereby corrected as shown below:

In the Specification

| | | |
|---|---|---|
| Column 5, | Line 37, | change "between V" to --between $\hat{V}$-- |
| Column 5, | Line 39, | change "denoted V" to --denoted $\hat{V}$-- |
| Column 9, | Line 40, | change "values V, taking" to --values $V_i$ taking-- |
| Column 9, | Line 54, | change "mesh in" to --mesh 3 in-- |
| Column 9, | Line 55, | change "observation zone," to --observation zone 1,-- |

In the Claims

| | | | |
|---|---|---|---|
| Claim 2, | Column 12, | Line 2, | change "$S_{opt}$, is" to --$S_{opt}$ is-- |
| Claim 2, | Column 12, | Line 13, | change "$V_i$, are" to --$V_i$ are-- |
| Claim 3, | Column 12, | Line 24, | change "$S_{opt}$, is" to --$S_{opt}$ is-- |
| Claim 3, | Column 12, | Line 37, | change "$s_i$, are" to --$s_i$ are-- |

Signed and Sealed this
Nineteenth Day of September, 2023

Katherine Kelly Vidal
*Director of the United States Patent and Trademark Office*